United States Patent [19]

Echols

[11] Patent Number: 5,081,447

[45] Date of Patent: Jan. 14, 1992

[54] KEEP OFF YOUR BACK ALARM

[76] Inventor: Wilford R. Echols, Box 170, Coahoma, Tex. 79511

[21] Appl. No.: 599,953

[22] Filed: Oct. 19, 1990

[51] Int. Cl.$^5$ .............................................. G08B 21/00
[52] U.S. Cl. ................................. 340/573; 128/782; 200/DIG. 2; 340/686; 340/689
[58] Field of Search ................. 340/573, 686, 689; 200/DIG. 2; 128/782

[56] References Cited

U.S. PATENT DOCUMENTS

| | | | |
|---|---|---|---|
| 3,631,438 | 12/1971 | Lewis | 340/573 |
| 3,795,240 | 3/1974 | Frank | 128/721 |
| 4,146,885 | 3/1979 | Lawson, Jr. | 340/573 |
| 4,433,693 | 2/1984 | Hochstein | 128/721 |
| 4,617,525 | 10/1986 | Lloyd | 340/573 |
| 4,696,307 | 9/1987 | Montgieux | 128/721 |
| 4,802,485 | 2/1989 | Bowers et al. | 128/633 |
| 4,972,177 | 11/1990 | Nolan | 340/573 |
| 5,008,654 | 4/1991 | Callaway | 340/573 |

Primary Examiner—Glen R. Swann, III
Attorney, Agent, or Firm—Marcus L. Bates

[57] ABSTRACT

Apparatus for influencing a person preferentially to sleep on his side and not on his back. A gravity actuated sensor apparatus is attached to a sleeping person for detecting body position and to sound an alarm informing the person when he is resting on his back; thereby enticing the person to sleep on one side or the other and not on his back. Appropriate circuitry connects the sensor apparatus and alarm so that the alarm is actuated in response to the sensor apparatus detecting an undesirable body position. The sensor apparatus is positioned on one's head, or alternatively, is positioned on one's body. The alarm can be sensed by a sleeper to thereby induce the sleeper to move to an alternate position whenever he attempts to rest on his back for more than a few seconds.

20 Claims, 2 Drawing Sheets

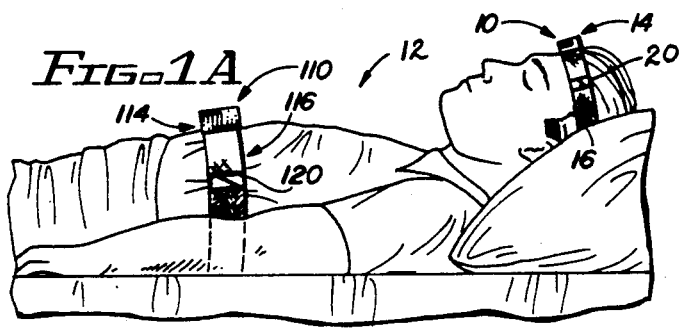
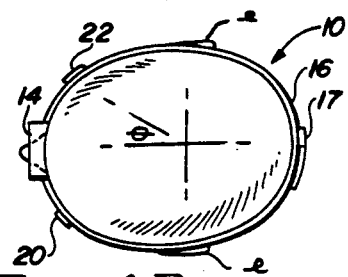
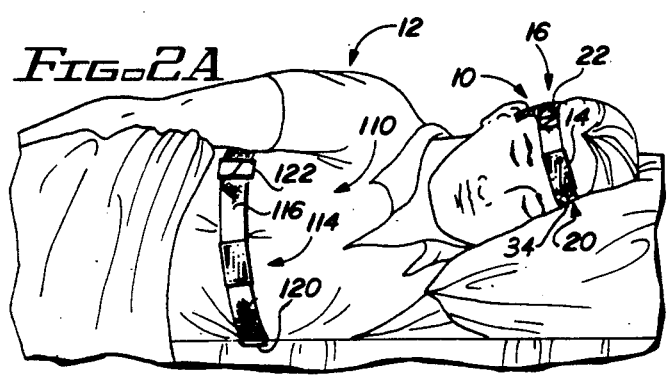
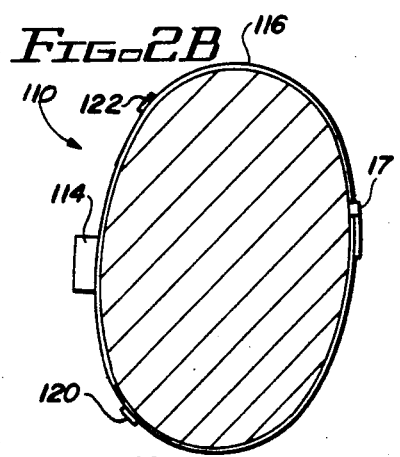
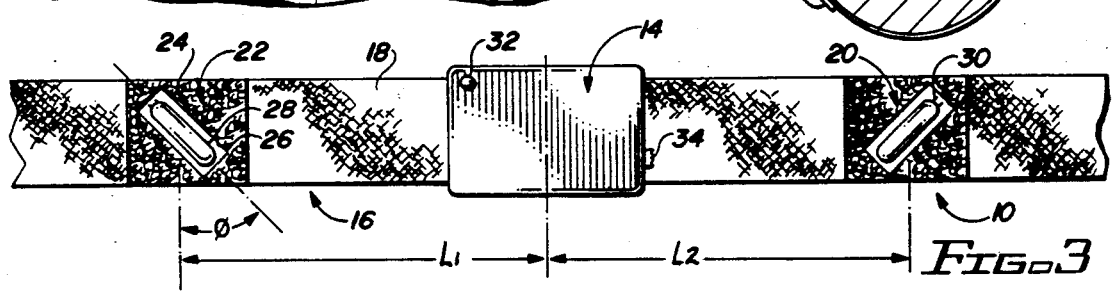
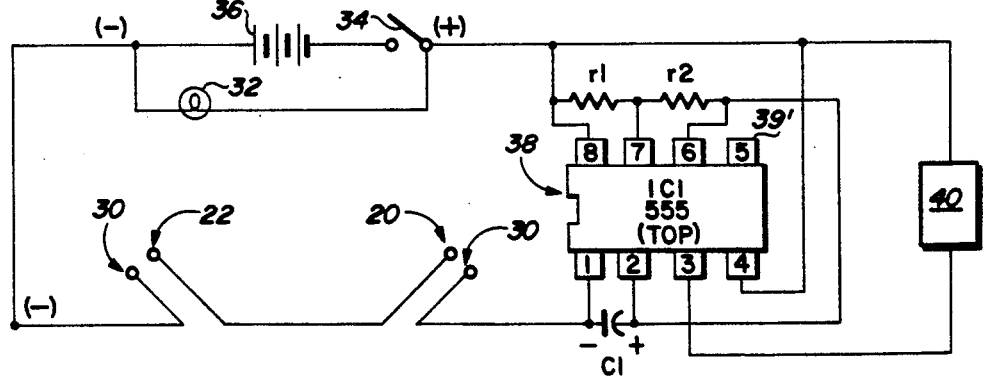

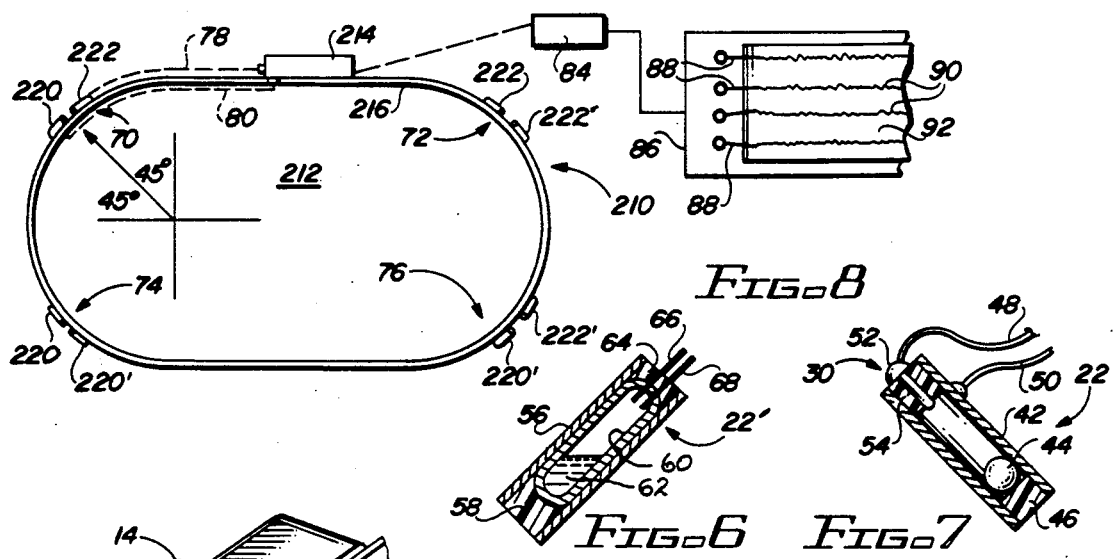
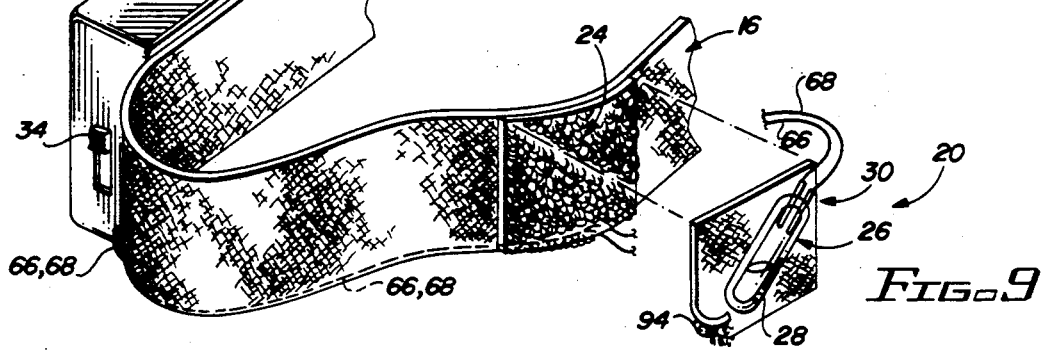
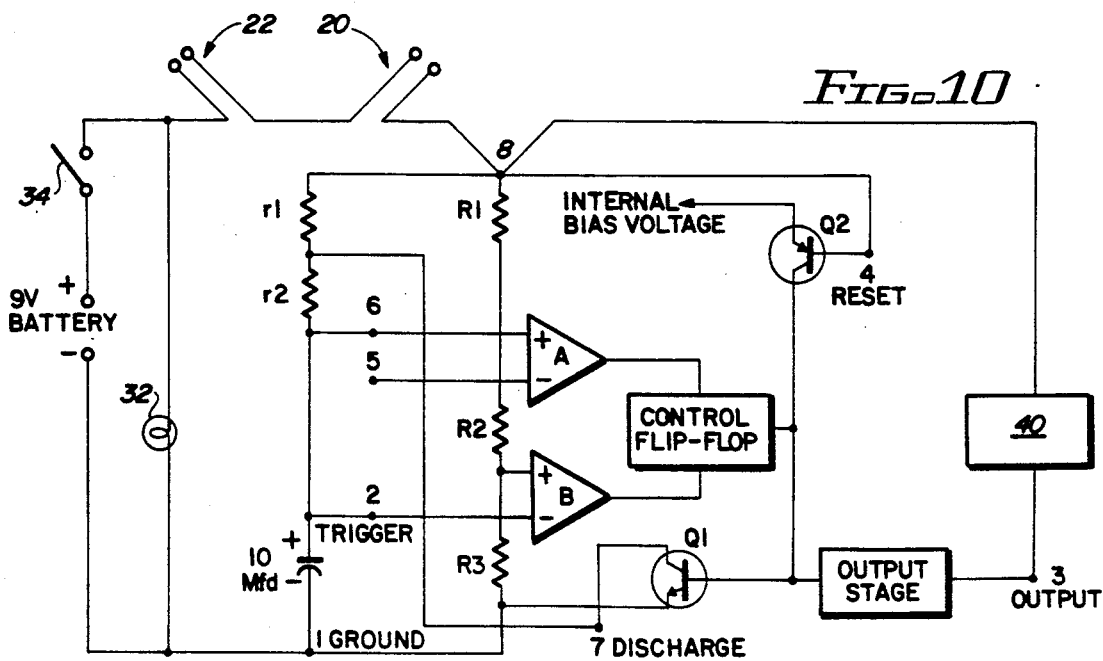

KEEP OFF YOUR BACK ALARM

BACKGROUND OF THE INVENTION

The present invention provides both method and apparatus for overcoming some sleep related problems, and more particularly, to solving the problem of how a person can avoid sleeping in an improper position. As evidenced by the references listed in the accompanying "Prior Art Statement", other methods and apparatus have been discovered and are available for dealing with the subject of body position during sleep, and reference is made to those patents for further background of this invention.

U.S. Pat. No. 4,617,525 describes apnea, a medical illness, in which people periodically stop breathing while sleeping; and defines apnea as a period of 10 seconds or greater duration of no respiration. The patent further points out that a person afflicted with apnea may be awakened several hundred times each night, while remaining unaware of their problem, and that episodes of repeated sleep apnea may take up practically the entire night.

The prior art indicates that a person suffering from sleep apnea may be in danger when inadvertently sleeping on his back because back sleepers are more prone to stop breathing. It would therefore be desirable to have made available a new and dependable method and apparatus for training a person to sleep in a position other than on his back, thereby eliminating many of the problems associated with sleep apnea.

Snoring is also considered a sleep problem, and aggravated cases of snoring can disrupt the sleep of both the sufferer as well as nearby persons. Snoring is a hindrance to good health due to restricted breathing and usually is associated with improper sleeping posture.

Special clinics are available for treatment of those suffering from sleep apnea; however, treatment may require an extended time spent under the care of expensive professionals and therefore the cost may be prohibitive to many.

Prior to the present invention, apparatus for teaching a person to sleep on his side rather than his back has been far too expensive and complex for the average person. Apparatus and method by which improper sleeping posture is avoided, and especially sleeping on the back is discouraged, is the subject of the present invention.

SUMMARY OF THE INVENTION

The present invention relates to method and apparatus for influencing a person preferentially to sleep on his side and not on his back. The invention comprehends apparatus worn by the person while sleeping, and includes an alarm for informing the person that he is resting on his back and that he should turn onto either of his sides in order to silence the alarm. The alarm is bothersome to the sleeper who soon teaches himself to change position by moving in an appropriate manner in order to eliminate the sensation produced by the alarm.

Broadly, the apparatus comprises a novel gravity actuated sensor apparatus for detecting body position, and circuitry that is connected to the sensor apparatus and to an alarm. The alarm is actuated in response to the sensor apparatus detecting an undesirable body position.

The sensor apparatus is secured to one's body, either attached on the head or on the chest, with the alarm being positioned to be sensed by a sleeping person to thereby induce the sleeper to change to an alternate position whenever he attempts to rest on his back.

More specifically, the sensor apparatus of the invention includes a right hand gravity actuated switch means and a left hand gravity actuated switch means; each arranged to be actuated by gravity and to be attached to the body at spaced locations, with one switch means being on the right and the other on the left frontal body region. Each switch means of the sensor apparatus is arranged at an appropriate angle respective to the vertical and the horizontal such that when a person rests on his back, both the right and left switch means are simultaneously gravity activated and thereby provide a signal to sound the alarm. However, when a person is resting on either of his sides, one of the two switch means will be in the inactive configuration and accordingly the sensor apparatus will not produce the signal, and consequently, the alarm is not actuated.

In one of the preferred forms of the invention, a right and left switch device is connected to appropriate circuitry, including an alarm, in such a manner that the alarm is sounded only when a person rests on his back for a time interval exceeding a few seconds, thus providing a reasonable interval of time during which the person can transition from his right to his left side, or vice versa, for example, this being a desirable expedient that should not be discouraged. However, the alarm is sounded should the person remain on his back rather than continuing the transition to his other side.

Another preferred form of the apparatus for influencing a person to sleep in a position other than on his back advantageously employs a sensor apparatus in the form of a pair of series connected gravity actuated switch means adapted to be attached in spaced relation on one's head at the frontal right and left hand portions of the head. Each switch means is arranged in the open circuit position at an angle of about 15 degrees respective to a horizontal plane when standing. The upper one of the switch means is open while the other or lower switch means is closed, and vise versa, when a person is laying down and rests on one or the other of his sides. Both switch means gravitate into the closed position when a person rests on his back, and thereby triggers the circuitry and sounds an alarm. This novel concept provides a unique sensor apparatus that is connected to circuitry for actuating an alarm, which under ideal conditions, is sublimely sensed at a level of perception that never completely awakens the sleeping person.

The novel sensor apparatus of this invention comprises a gravity actuated signal producing means that includes right and left switch means adapted to be supported on the right and left sides of one's body or head in spaced relationship respective to one another, whereby, when a person is resting on his back, the right and left switch means are concurrently actuated to produce a signal, whereupon the circuitry actuates an alarm; and when a person rests on either side, one of the switch means fails to produce a signal, and no alarm is sounded.

Still more specifically, with this invention, a gravity actuated right and left switch means is adapted to be supported on the right and left sides of one's body or head in spaced relationship respective to one another, and when a person is resting on his back, the right and left switch means are concurrently actuated to produce a signal which triggers appropriate circuitry and actuates an alarm; and when a person rests on either side, the upper one of the switch means fails to produce a signal, and no alarm is sounded.

Therefore, a primary object of the present invention is the provision of an alarm apparatus for influencing a person to sleep in a position other than on his back.

Another object of the present invention is the provision of method and apparatus for training or influencing a person preferentially to sleep on his side and not on his back.

A further object of the present invention is the provision of a sensor apparatus that comprises gravity actuated switch means, electrical circuitry, and an alarm; all of which is adapted to be worn on one's body while sleeping, with there being a switch means situated on the right and left side of the body in spaced relationship respective to one another, whereby, when a person is resting on his back the right and left switches are simultaneously actuated to produce a signal, whereupon the electrical circuitry actuates an alarm; and when a person rests on either side, only one of the switches is actuated and the sensor apparatus produces no signal, so the alarm is not actuated.

A still further object of the present invention is the provision of a sensor apparatus that includes a pair of gravity actuated switch means, electrical circuitry, and an alarm, all of which is adapted to be worn on one's body while sleeping, with there being a right and a left switch means situated in spaced relationship and series connected respective to one another, with each switch means being located against the head at a location between the eye and the ear, whereby, when a person is resting on his back, the right and left gravity actuated switches are simultaneously actuated to produce a signal, whereupon the electrical circuitry actuates the alarm; and when a person rests on either side, only the lower switch of the pair of switches is actuated and the sensor device produces no signal, so the alarm is not actuated.

These and other objects and advantages of the present invention will become readily apparent to those skilled in the art upon reading the following detailed description and claims and by referring to the accompanying drawings.

The above objects are attained in accordance with the present invention by the provision of method for use with apparatus fabricated in a manner substantially as described herein.

BRIEF DESCRIPTION OF THE DRAWINGS

FIG. 1A is a fragmentary, side elevational view of a person resting on his back while wearing apparatus made in accordance with the present invention;

FIG. 1B is an end view of the person seen in FIG. 1, having apparatus made in accordance with the present invention attached thereto;

FIG. 2A is a fragmentary view of the person seen in FIG. 1A, resting on his side, with apparatus made in accordance with the present invention being disclosed therewith;

FIG. 2B is an end view of the person seen in FIG. 2A, with apparatus made in accordance with the present invention associated therewith;

FIG. 3 is a fragmentary, detailed view of part of a preferred embodiment of the apparatus disclosed in the foregoing figures;

FIG. 4 is a top end view of the apparatus disclosed in FIG. 3;

FIG. 5 is a schematical representation of circuitry for use in conjunction with the present invention;

FIG. 6 is an enlarged, longitudinal cross-sectional view of part of the apparatus disclosed in the foregoing figures;

FIG. 7 is an enlarged, longitudinal cross-sectional view that sets forth a modification of the apparatus disclosed in FIG. 6;

FIG. 8 is a part diagrammatical, part schematical, fragmentary representation of another embodiment of the present invention;

FIG. 9 is a broken perspective view of part of the apparatus disclosed in FIGS. 1, 2, 3 and 4; and, FIG. 10 is a schematical representation of some of the circuitry for use in FIGS. 3, 4 and 9.

DETAILED DESCRIPTION OF THE PREFERRED EMBODIMENT

The present invention provides both method and apparatus for overcoming several serious sleep related problems, and more particularly, for solving the problem of snoring and apnea by encouraging a person to avoid sleeping in an improper position.

In the figures of the drawings apparatus 10 is attached to a person 12 for influencing the person preferentially to sleep on his side, as shown in FIG. 2A, and not on his back, as shown in FIG. 1A. The apparatus 10 is suitably affixed in the illustrated manner to a person's forehead and includes a control box 14 having circuitry therein. The box is frontally mounted in supported relationship by a suitable adjustable strap device 16 that circumferentially extends about the head. Adjustment means 17 comfortably selects an appropriate size of the apparatus 10.

The strap 16 has an outer surface 18 to which there is attached a sensor apparatus comprising a pair of gravity activated sensors, preferably in the form of a switch means 20 and 22, arranged in spaced apart relationship and equally spaced from the circuitry containing control box 14. For convenience, the gravity actuated sensor means 20 and 22 are arranged on opposed sides of the before mentioned control box 14, as will be more fully described later on.

As best seen in FIGS. 3 and 4, the gravity activated switch means 20 and 22 are adjustably positioned in a mounted relationship on the outer surface 18 of support or strap 16. Preferably, Velcro fastening material 24 is applied to the outer surface of a medial length of the strap and to the inner surface of a rectangular sensor support 26, thereby removably affixing support 26 to the Velcro fastening material 24. In FIGS. 3 and 4, each gravity actuated sensor apparatus 20 and 22 comprises an elongated tubular member 28 suitably mounted to support 26. While any suitable known gravity actuated sensor means can be used at 20 and 22, a simple, satisfactory sensor apparatus in the form of a switch means is shown in greater detail in FIGS. 6 and 7 for purposes of illustration, and to enable a better comprehension of the inventive concept to be gained.

In the preferred embodiment of the invention, the gravity actuated sensor apparatus is a switch means, 20 and 22, having a longitudinal axial centerline arranged at an angle selected from a range of angles respective to the vertical and horizontal. The upper terminal end of each of the switch means is provided with suitable conductors 30 for connection into the circuitry, as shown in FIGS. 5 and 10. The circuitry includes a pilot light 32 and a main power switch 34.

In FIGS. 1A, 2A and 2B there is additionally disclosed another embodiment 110 of the invention, wherein like or similar numerals refer to like or similar elements of the preferred embodiment 10 of the invention. The apparatus 110 includes a control box 114 having circuitry therein and suitably mounted to a support belt or strap 116. The support belt circumscribes a person's chest or midsection and is comfortably worn centered over the lower sternum or chest, and includes a pair of gravity actuated switch means 120 and 122 attached in spaced relationship on opposed sides of the centrally located control box 114.

In FIG. 3, L1 and L2 indicate the spacing of the switch means 20 and 22 respective to one another and to circuitry 14. As noted, the switch means can be moved apart within an operating range to select the sensitivity of the apparatus. The support 16 of FIG. 3 is shown in a flat rather than a curved configuration for the purpose of better illustrating this embodiment of the invention.

In FIG. 5, a power supply 36 is schematically illustrated in conjunction with pilot light 32, power switch 34, and the gravity actuated switch means 20, 22. Integrated circuitry 38 is contained within circuit 14 and is connected as shown, and additionally includes capacitor C1, resistor R1, and resistor R2, the values of which may be changed in order to change the operation thereof. Numeral 39' indicates one of 8 terminals by which other electrical components can be connected to circuit 38. The integrated circuit 38 is identified as ICI 555 and is commercially available. The capacitor C1 preferably a 10 microfarad condenser while resistors R1 and R2 are 75 k ohms, and 348 k ohms, respectively. The values of C1, R1, and R2 are varied to achieve different time cycles of operation, in a manner known to those skilled in the art.

An alarm 40 is connected across the switched power supply and terminal 3 of the circuit 38, so that closure of the switch connects one side of the alarm to the power supply. The circuitry 38 connects terminal 3 to the power supply 36 upon closure of both switch means 20 and 22.

In FIG. 7, one form of the gravity activated sensor apparatus is a switch means 22 having a metallic cylindrical housing 42 within which a metal ball 44 is captured in close tolerance relationship therewith. The ball 44 is illustrated resting against insulator 46 and in electrical contact with wall 42. Conductors 48 and 50, respectively, are connected to switch contacts 52 and 42, respectively. Switch contact 52 extends through the illustrated insulator at 54 where the inner terminal end thereof can make electrical contact with conducting ball 44 and thereby connect conductors 48 and 50 so that current flows therebetween when the switch means is tilted or inclined to move the ball 44 against the contacts at 30. This closure of sensors 20 and 22 provides a signal for circuitry 14.

In the gravity activated switch means 22' of FIG. 6, an outer housing 56 is closed at 58 and encloses mecury switch 60 therein. The usual blob of mercury 62 has gravitated to nonconducting end 58 which is opposed to the conductor end. The conductor end has an insulator 64 which receives switch contact 66 and 68 therethrough, whereby, when switch means 22 is tilted or inclined in the opposite or alternate position, the mercury gravitates into end 64 and shorts contacts 66 and 68, thereby permitting current to flow therethrough. This closure of switch 22', when arranged with respect to the other switch 20 as taught herein, provides a signal for circuitry 14 when both switches gravitate into the closed position.

In FIG. 9, the gravity actuated switch means 20 has been pulled or temporarily removed from the co-acting Velcro fastener material 24. Conductors 66 and 68 extend along the lower edge portion of strap 16 and are connected to circuitry 14 by any suitable connector device at the ends of conductors 66, 68. The fastener material 94 applied onto the confronting surface of the sensor support 26 can be the "hooks", and the "loops" can be applied to the strap, so that support 26 can be placed on the Velcro fastening material 24 to adjustably locate the switch means 22 at any desired position within a range of positions.

In the alternate embodiment or sub-combination disclosed in FIG. 8, pairs of gravity activated sensor apparatus are supported on belt 216 and arranged at each of the illustrated 45 degree positions 70, 72, 74 and 76; with the pairs of sensor apparatus each being placed in spaced relationship but closely adjacent to one another. Each of the gravity actuated sensor apparatus of the pairs 70-76 are similarly arranged as previously seen at 20 and 22 in FIG. 3, for example. Each sensor apparatus is connected to suitable circuitry that is housed in control box 214. Numerals 78 and 80 indicate one of the conductors leading from one of the pairs of sensor apparatus 70 to a transmitter device 214. The other sensors 72-76 have similiar conductors connected thereto.

Receiver means 84 receives a signal from circuitry 214. Chart device 86 has a plurality of pins 88 providing a curve in the form of indicia 90, 92 related to the position of each of the pairs of gravity actuated switches 70-76.

The individual pairs of switches are arranged to provide circuits at 220; 222; 220'; and 222'. These four circuits are arranged to provide four different input signals to the recorder 86. Each circuit at 220, 220; 222, 222; 220', 220'; and 222', 222' are arranged to have pairs of switches at 70-76 that are located approximately 45 degrees respective to a pair of perpendicular planes passing longitudinally through the body as noted in FIG. 8, for example. The switches 220, 220 are connected together and to the circuit means to provide a signal from which a curve is derived at 90. Switches 220', 220'; 222, 222; and 222', 222' are similarly arranged to provide a circuit, each of which provides a signal for a curve 90.

FIG. 10 shows additional details of the circuitry 38 of FIG. 5 wherein the terminals 1-8 of FIG. 5 are more detailed, and other additional details are disclosed to enable the preferred form of the invention to be easily fabricated and more fully appreciated.

The head band embodiment exemplified by apparatus 10 of the invention is worn on the head in the same position as a hat or cap band. Each of the two gravity actuated switch means 20 and 22 is mounted between the front corner of the head and the ear, there being a switch means located on each side, that is, rearwardly of the eye and toward the ear, depending on the particular shape of the individuals head. The geometry of the head and the location of the sensor apparatus cause the switch means to be brought into parallel relationship respective to one another as the switch means are progressively moved away from one another and toward the ears; and, as the switch means approach a parallel relationship, their contact actuator no longer gravitates in any particular direction; i.e.; gravity acts with equal force in all directions when the contact actuator is in a horizontal plane. Hence the sensor apparatus becomes progressively more sensitive as the switch means are moved away from one another and toward the ears, and are most sensitive when placed as far back as possible on the sides of the head before they reach a parallel relationship. The switch means must not be placed too far back, so as to approach too closely to being parallel to each other, when viewed from the top of the head while being worn by the person, for reasons noted above. It is critical that both sensors or switch means 20, 22 assume the active or alarm position when one rests on the back, and to assume the inactive or non-alarm position when one rests on either side.

Velcro mounted sensors allow adjustment of switch location at L1 and L2 to accommodate different shaped heads. These sensors, when mounted on a standing person, preferably point downward at about a 15 degree angle respective to the horizontal with the switch being in the open-contact position, and with the upper end of the switch (the contact end) pointing toward the back of the head on each side. The 15 degree angle can be changed considerably, as far example, 10–20 degrees. However 15 degrees allows a person to walk around or sit, without causing the alarm to sound, because the contacts of the switches remain in the open position. This angle of 15 degrees also prevents a person lying on their back from turning their head to one side sufficiently to avoid closure of the switches to thereby avoid sounding the alarm. Hence arrangement of each of the switches 20, 22 at 15 degrees when standing, and less than 180 degrees (not parallel) when viewed from the top provides the optimum switch position in the vertical and horizontal planes.

The master switch, pilot lamp (to prevent being left on), electronic components, battery, and alarm unit is housed in the illustrated control box (at 14) and is attached to the head band in the front center position. Where the alarm unit is of the vibrating type, extending it through the head band to make contact with the forehead is found desirable. The alarm unit is silent when using a small D.C. motor with an off-set weight, near silent when using an electronic buzzer without a noise-making diaphragm, or audible when using an electronic buzzer.

The chest-belt embodiment 110 of the invention is worn around the lower chest, such that the control unit box 114 will be centered over the lower sternum. The two sensor switch means 120 and 122 are mounted on the chest-belt at the front to side corner positions of the chest, as shown in FIGS. 1A, 1b, and 2B. These sensors do not require the sensitivity of the headband model, which is complicated by the requirement of monitoring the back-sleeping position by the position of the head. The sensors otherwise work on the same operating principle as the apparatus 10 of FIGS. 1A and 1B.

Sensors 20, 22 and 120, 122 are each velcro-mounted in order to allow adjustment respective to the front corner position of the chest as seen in FIG. 2b. The switch means of the sensor apparatus 110 point downward at a 25 to 45 degree angle from the horizontal when standing and are arranged in the open-switch position with the contact end 66, 68 or 48, 50 of the open switch 22 or 22' oriented to point upward toward the back on each side, so that the switch is in the open position when standing and closed position when on the back. The 25 to 45 degree range of the switch angle allows a person to walk around or sit, without causing the switch contacts to close and the alarm to sound. The control box containing the master switch, pilot lamp, electronic components, battery, and alarm unit is attached to the chest-belt in the front center position. When the vibrating alarm unit is used, it can extend through the back of the control unit to make contact with the sternum. The alarm unit will be silent when using a small D.C. motor with off-set weight, near silent when using a pulsing electronic controlled solenoid coil, or audible when using an electronic buzzer, as in the before described example of the embodiment 10.

Should a person wearing either of these embodiments turn to the back-sleeping position and remain there, both sensor switch means 20, 22 or 120, 122 will be moved to the closed position. Closure of both switches applies the power source 36 across the circuitry 38 and starts the charge time for the on-off cycle timer, which preferably is five seconds. If the person continues turning from side to side, the switch means of the sensor apparatus will not be closed long enough to charge the timer sufficiently to begin the on-off alarm cycle. Thus, if a person pauses too long while in the back position, he is quickly and briefly urged to continue turning without being awakened. The person soon learns to turn from side to side without stopping in order to avoid the alarm cycle. A brief alarm cycle of approximately two seconds on followed by four seconds off, with this timed cycle continuing until the person turns to rest on either side, has proven to be most effective as this arrangement seldom causes a person to be fully awakened.

While it is preferred that sensor switch means 20, 22 be placed at a location between the eye and the ear as shown, it is possible, but impracticable, to place the switch means equidistant from one another and behind the ears.

As best described in conjunction with FIG. 3, switch means 20, 22 preferably are arranged, when standing, at an angle of approximately 75 degrees respective to the vertical or 15 degrees respective to the horizontal, and this angle can be changed, if desired, so long as the uppermost switch, when in the position of FIG. 2a, opens while the lower switch closes; and, when in the position of FIG. 1a, both switches close. The sensitivity of the apparatus is changed by adjusting L1 and L2 as taught in FIG. 9 by separating support 26 from the underlying velcro fastener material and relocating the support to achieve any desired sensor sensitivity. It is critical to the invention that switch means 20, 22 be placed respective to the head whereby they both (almost but not necessarily simultaneously) are moved into a first position of operation (which is the signal producing or activated position of operation) when the sleeper is resting on his back, and that at least one of the switches is moved into a second position of operation (which is the inactivated position of operation wherein no signal is produced) when one is resting on his side. It is possible to adjust the relationship of the two switches respective to one another and to one's body so as to achieve this configuration of the sensor apparatus as previously noted so that proper operation of the invention is always enjoyed.

The actual cross-sectional configuration of different people will vary, therefore the oblated illustration of the support seen in FIGS. 1B, 2B, and 8 is not necessarily the actual configuration of a specific person, but instead is a diagrammatical or schematical representation thereof.

The simplest form of the sensor apparatus is any gravity operated switch means and is shown by way of example in FIGS. 6 and 7, wherein a gravity actuated switch means is in the non-conducting or second configuration when inclined respective to the horizontal and which is moved into the conducting or signal producing configuration when inclined into an opposite relationship respective to the horizontal.

In operation of FIGS. 1-4, when utilizing the switch means of either of FIGS. 6 and 7, for example, the lower one of the switch means 20, 22 will be closed while the other or upper switch will be open, regardless of which side a person is resting on. However, both the switch means 20 and 22 will assume the closed or signal generating or actuated position when a person rests on his back, as seen in FIG. 1A, for example. Accordingly, when a person is changing position from his left to his right side, the switch means will both momentarily be simultaneously closed, but there is no need to sound the alarm because the person is merely changing sides, which is desirable. Therefore, there is an interval of time provided by circuitry 38 before alarm 40 is sounded in order to not discourage the person from changing sides. It is important, however, that when the person changes position from one side and comes to rest on his back, that the alarm 40 is activated after several seconds have lapsed, thereby signaling the person that he is in an improper position. As soon as the person moves from his back to either side, the alarm is silenced.

It is interesting to note that the upper switch means is always open and that the lower switch means is always closed when a person is resting on his side, and that the lower switch means remains closed as a person moves from his side onto his back; and that the other or upper switch means also closes as the person moves onto his back, thereby placing both switch means in the conducting or closed position whereupon a current flow path is provided that triggers the circuitry and sounds the alarm.

The alarm preferably is any means that can be suitably perceived by one's senses, and of a magnitude to make the person aware of his improper position. The alarm should present a persistent low level annoyance to the sleeper; but it should not awaken him if he responds thereto by changing position within a few seconds interval of time.

It has been found that the apparatus of the present invention will train a person not to sleep on his back, and that the sleeper has no recollection of being subjected to the alarm. A few nights rest using the apparatus of the present invention results in a person favorably responding to the alarm as his responses are progressively conditioned by the apparatus so that the ill effects of apnea and snoring is overcome, and moreover, the tendency to sleep on one's back diminishes as he continues to receive training from the apparatus.

The circuitry contained in control box 14 and switch means 20, 22 can be mounted to the head in a number of different manners, while remaining within the scope of the claimed invention. While it is preferred to mount the apparatus to the head, in many instances, for one reason or another, it will be more desirable to mount the apparatus in proximity of the abdomen or chest, as shown in FIGS. 1A, 2A, and 2B.

It is also considered within the comprehension of this invention to directly support switch means 20, 22 and circuitry at box 14 to the forehead by special adhesives and the like. Moreover, the circuitry and sensor apparatus can be suitably incorporated within a light weight frame in a manner similar to eyeglasses, or incorporated into a nightcap where one finds the illustrated mount means objectionable.

The alarm, if initially ignored, could be arranged to grow in intensity until the person is fully awakened and consciously elects to turn from his back onto a side sleeping position. The alarm can be an audible sound of low intensity, a sensation of a vibratory nature, an electrical impulse of suitable intensity and growing magnitude, or a combination thereof.

I claim:

1. Apparatus for training a person to sleep in a position other than on his back, comprising:
    a gravity activated sensor apparatus adapted to be supported on the body for generating a signal when a person is resting on his back; there being a right hand gravity activated sensor and a left hand gravity activated sensor that is responsive to and moves from a non-signaling position into a signaling position;
    said right and left hand sensors are oriented respective to one another to assume the signaling position when the person rests on the back;
    an alarm for informing a person that he is resting on his back;
    circuitry for actuating said alarm in response to receiving a signal simultaneously from said right and left hand sensors.

2. The apparatus of claim 1 wherein said right and left hand sensors are adapted to be attached to the body at spaced locations on the right and left frontal body regions;
    each said sensor is arranged at an angle respective to the vertical and horizontal such that when a person rests on his back, both the right and left hand sensors are gravity actuated into a signal producing position and thereby sound said alarm.

3. The apparatus of claim 1 wherein said right and left sensors are switch means connected in series and to said circuitry in such a manner that said alarm is sounded only when a person rests on his back and thereby simultaneously moves both switch means into the signal producing position.

4. The apparatus of claim 1 wherein said right and left hand sensors are series connected switch means adapted to be attached in spaced relation on the frontal right and left hand portions of the body with said switch means each being arranged respective to a vertical plane whereby one of said switch means is open while the other switch means is closed when a person rests on his side and both switch means are closed when a person rests on his back.

5. The apparatus of claim 1 wherein said right and left hand sensors are gravity actuated switch means adapted to be supported on one's body in spaced relationship respective to one another whereby when a person is resting on his back, the right and left hand sensors are actuated to produce a signal, whereupon said circuitry actuates said alarm; and when a person rests on either side, one of said switches remains in the non-signaling position and the apparatus fails to produce a signal.

6. Apparatus for training a person to sleep in a position other than on his back, comprising:
    a sensor apparatus that includes a right hand gravity activated sensor means and a left hand gravity activated sensor means, each sensor means being movable from a first signal producing position into a second position in which no signal is produced;

means for mounting the right and left hand sensor means on a person's body and orienting said sensor means respective to one another to assume the first signal producing position when the person rests on his back, and for one sensor means to assume the second position when the person is not resting on his back;

an alarm for informing a person that he is resting on his back; and, circuitry for actuating said alarm in response to receiving a signal simultaneously from the right hand and left hand sensor means.

7. The apparatus of claim 6 wherein said circuitry includes means for providing a delay of several seconds before sounding said alarm.

8. The apparatus of claim 6, wherein said sensor apparatus is mounted on one's head and wherein said alarm can be sensed by a sleeper to thereby induce the sleeper to move to an alternate position.

9. The apparatus of claim 6, wherein said sensor apparatus is mounted on one's chest and wherein said alarm can be sensed by a sleeper to thereby induce the sleeper to move to an alternate position.

10. The apparatus of claim 6 wherein said right and left hand sensor means is connected to said circuitry in such a manner that said alarm is sounded only when a person rests on his back in excess of several seconds, and after a person moves to a position other than on his back, one of the right and left hand sensor means is moved to the second position and the alarm is silenced.

11. The apparatus of claim 6 wherein said sensor apparatus is a pair of series connected switch means adapted to be attached in spaced relation on the frontal right and left hand portions of the body, with said switch means each having an actuator means that is arranged at an angle respective to a vertical plane whereby one of said switch means is open while the other switch means is closed when a person rests on his side and both switch means are closed when a person rests on his back.

12. The apparatus of claim 6 wherein said sensor apparatus comprise gravity actuated switches adapted to be supported on one's body in spaced relationship respective to one another whereby when a person is resting on his back the right and left switches are actuated to produce a signal, and wherein said circuitry actuates said alarm when the signal is present for several seconds;

and when a person rests on either side, one of said switches fails to produce a signal.

13. The apparatus of claim 6 wherein the right and left hand sensor means are moved into the first position when inclined at a first angle respective to the body, and said sensor means are moved into the second position when inclined at an opposite angle respective to the body; said right and left hand sensor means are adapted to be attached to the body at spaced locations on the right and left frontal body regions such that the right hand sensor means is in the first position when the person rests on the right side and is in the second position when the person rests on the left side;

and said left hand sensor means is in the first position when the person rests on the left side and is in the second position when the person rests on the right side;

whereby, each said right and left hand sensor means is arranged at an angle respective to the vertical such that when a person rests on his back, both the right and left hand sensor means are actuated into the first position and thereby sound said alarm.

14. The apparatus of claim 6 wherein said right and left sensor means are connected in series and to said circuitry in such a manner that said alarm is sounded only when a person rests on his back, and thereby moves said right and left sensor means into an actuated configuration.

15. The apparatus of claim 6 wherein said right and left hand sensor means are series connected switch means adapted to be attached in spaced relation on the frontal right and left hand portions of the body between the eyes and the ears, with said switch means each being arranged at an angle respective to a person's head whereby one of said switch means is open while the other switch means is closed when a person rests on his side and both switch means are closed when a person rests on his back.

16. Method of encouraging a person to sleep in a position other than on his back, comprising the steps of:

attaching a right hand and left hand gravity activated sensor means to the body of a person for generating a signal indicating when the person is resting on his back; mounting the right hand sensor means to provide a signal when in a first position; and mounting the left hand sensor means to provide a signal when in a first position;

orienting said right and left hand sensor means respective to one another to assume the first position when the person rests on his back; and for one of said right and left hand sensor means to assume a second position in which there is an absence of said signal when the person rests on his side;

providing an alarm for informing a person that he is resting on his back; and actuating said alarm in response to receiving a signal simultaneously from said right and left hand sensor means.

17. The method of claim 16, and further including the steps of attaching said right and left hand sensor means to the body at spaced locations on the right and left frontal body regions;

arranging each of said right and left hand sensor means at an angle respective to the vertical such that when a person rests on his side; one of the right and left hand sensor means is gravity actuated into said second position and the other of said right and left hand sensor means is gravitated into the first position.

18. The method of claim 16, and further including the steps of connecting said right and left hand sensor means in series and to a circuitry means in such a manner that said alarm is sounded only when a person rests on his back and thereby simultaneously moves both the right and left hand sensor means into the first position.

19. The method of claim 16, and further including connecting said right and left hand sensor means in series and attaching said right and left hand sensor means in spaced relation on the frontal right and left hand portions of the body; arranging the right and left hand sensor means at an angle respective to a vertical plane whereby one of said sensor means is open while the other sensor means is closed when a person rests on his side and both said right and left hand sensor means are closed when a person rests on his back.

20. Apparatus for monitoring a person's sleeping habits, comprising;

a sensor apparatus for detecting body position;

a recorder means for storing data related to sleeping habits;

circuitry connected to said sensor apparatus and to said recorder means by which said recorder means is actuated in response to said sensor apparatus detecting a body position indicating the position a person is resting;

said sensor apparatus includes a plurality of signal producing means; each said signal producing means being arranged to be actuated by gravity and to be attached to the body at spaced locations on the right and left frontal and rear body regions;

each said signal producing means is arranged at an angle respective to the vertical and to the horizontal such that when a person rests on his back some of the signal producing means are gravity actuated and thereby provide a signal, and when a person rests other than on the back, only one of the signal producing means is actuated and provides a signal.

* * * * *